United States Patent [19]

Anahara et al.

[11] 4,050,225
[45] Sept. 27, 1977

[54] PROCESS AND APPARATUS FOR MEASURING FALSE TWIST IN THERMOPLASTIC SYNTHETIC YARN

[75] Inventors: Meiji Anahara, Kyoto; Takayoshi Fujita, Takatsuki, both of Japan

[73] Assignee: Toyo Boseki Kabushiki Kaisha, Osaka, Japan

[21] Appl. No.: 551,782

[22] Filed: Feb. 21, 1975

[51] Int. Cl.² .............................................. D01H 13/32
[52] U.S. Cl. ................................. 57/34 HS; 57/34 R; 57/157 TS
[58] Field of Search ................. 57/1 R, 34 R, 34 HS, 57/77.3, 77.4, 156, 157 TS; 73/160; 226/100; 324/178

[56] References Cited

U.S. PATENT DOCUMENTS

| | | | |
|---|---|---|---|
| 3,303,419 | 2/1967 | Gith | 73/160 X |
| 3,405,556 | 10/1968 | Gonsalves et al. | 73/160 |
| 3,510,632 | 5/1970 | Standberg | 324/178 X |
| 3,550,400 | 12/1970 | Peat et al. | 324/178 X |
| 3,613,347 | 10/1971 | Carruthers | 73/160 X |
| 3,667,292 | 6/1972 | Hada | 73/160 |
| 3,705,487 | 12/1972 | Carruthers | 57/77.4 |

OTHER PUBLICATIONS

Egambaram et al., "Heat Transfer in False Twist Texturing"; Textile Research Journal; Oct. 1974; (p. 807).

Primary Examiner—Richard C. Queisser
Assistant Examiner—Charles Gorenstein
Attorney, Agent, or Firm—Burgess, Ryan and Wayne

[57] ABSTRACT

A yarn of thermoplastic synthetic fibers is false twisted and during the false-twisting operation the number of false twists being imparted to the yarn is estimated with high accuracy. The estimation of the number of false twists is carried out by measuring, in a section within the twisting zone of the false-twisting apparatus, the speed of the yarn being processed under a normal operational condition and by the estimated number of false twists the yarn is advantageously quality controlled.

13 Claims, 11 Drawing Figures

PROCESS AND APPARATUS FOR MEASURING FALSE TWIST IN THERMOPLASTIC SYNTHETIC YARN

The invention relates to a process and apparatus for false-twisting a thermoplastic synthetic yarn, more particularly relates to a process and apparatus for false-twisting a thermoplastic synthetic yarn wherein the number of false twists being imparted to the yarn is estimated with high accuracy.

BACKGROUND OF THE INVENTION

In false-twisting of a yarn of thermoplastic synthetic fibers, false twist is imparted to the yarn by a false-twisting means. As the false-twisting means, a false-twisting spindle unit is conventionally used because false twists of a number closely corresponding to a predetermined number of twists can be comparatively easily and stably obtained by the false-twisting spindle unit. In such a case, however, differences in the number of false twists may occur along the length of the yarn and/or between two or more of the spindles. In general, it has recently been a practice, in order to increase the processing speed of the false-twisting, that false twist is imparted to a thermoplastic synthetic yarn by using a friction type false-twisting unit or a fluid jet type false-twisting unit. Particularly in the case where the friction type or fluid type false-twisting unit is used, it is very difficult to detect and control the differences in number of twists along the yarn length or between two or more of the false-twisting means. This is because of the difficulty in ensuring that the yarn is twisted a particular number of twists corresponding to a predetermined number of twists and, thus, in determining the number of false twists being actually imparted to the yarn.

For the determining number of twists of a yarn being false twisted, some conventional methods have been utilized. One of the methods is a direct method wherein a yarn in the twisting zone of a false-twisting apparatus is taken out and the number of twists actually imparted to the yarn is measured by a twist counter. In this direct method, the actual number of twists can be determined approximately accurately, but this method has the drawbacks that the production operation has to be temporarily discontinued to take out the yarn by cutting the yarn being processed and that it is difficult to detect the minute variations in the number of twists along the length of the yarn.

A method of indirectly determining the number of twists of a yarn during a false-twisting operation has been proposed in Japanese Patent Publication No. 38-24769. In this method, the determination of the number of twists is effected by bringing a disc in contact with the yarn in the twising zone in a condition such that the axis of the yarn is parallel to the rotational axis of the disc, rotating the disc by frictional force, counting the number of rotations of the disc and estimating the number of twists from the number of rotations. This method has, however, the drawbacks that noticeable error easily appears due to slippage or differences in the quality or quantity of the applied oils, abnormal yarn rotation occurs when the disc is brought in contact with or removed from the yarn and, in addition, an unusual number of yarn rotations often occurs, due to the loss of rotational energy of the yarn, during the time the disc is in contact with the yarn. An improved method wherein the above-stated energy loss is intended to be decreased has been proposed in published Japanese Patent Application No. 49-13463. This method has also drawbacks similar to those mentioned above.

A further method has been proposed in Japanese Patent Publication No. 41-17942, wherein the determination of number of twists is effected by measuring the frequency of two-dimensional vibration in the direction perpendicular to the progressive direction of the yarn being processed. The drawbacks of this method are that the results are effected by various factors such as the tension, speed and thickness of the yarn and the length of the twisting zone and, thus, are inferior in accuracy and reproducibility. This method has a further drawback that a large scale apparatus is needed for the determination.

As hereinbefore described, in conventional false-twisting methods it has been very difficult to detect and control the differences in the number of false twists along the yarn length or between two or more of the false-twisting mens by determining the number of false twists being actually imparted to the yarn.

SUMMARY OF THE INVENTION

The principal object of the invention is, accordingly, to provide a process and apparatus for false-twisting a thermoplastic synthetic yarn wherein the number of false twists being actually imparted to the yarn can be easily and accurately determined.

In accordance with the invention, there is provided, for attaining the aforesaid object, a process for false-twisting a thermoplastic synthetic yarn wherein a yarn of thermoplastic synthetic fibers is fed through a feed roller, the fed yarn is false twisted by a false-twisting means while being heated and optionally being drawn and, then, the false twisted yarn is taken up through a delivery roller, which process comprises measuring, in a section within the twisting zone formed inbetween the feed roller and the false-twisting means, the speed of the yarn being processed under a normal operational condition to estimate the number of false twists actually imparted to the yarn by determining the twist shrinkage of the yarn in said section from the measured yarn speed and the speed of the yarn being processed under the same condition as said normal operational condition but without twisting, which is measured in the same section as that wherein said speed of the yarn being processed under the normal operational condition has been measured and, then, converting the determined twist shrinkage into a relationship between number of twists and twist shrinkage, which has previously been determined for the yarn to be processed.

The process of the invention may further comprise controlling the number of false twists being imparted to the yarn by regulating the difference between the predetermined number of false twists and the estimated number of twists.

Further, according to the invention, there is provided an apparatus for the practice of the above-mentioned process.

The above and other objects and features of the invention will be clear from the description given hereinafter with reference to the accompanying drawings.

DETAILED EXPLANATION OF THE INVENTION

The invention is based on the discovery that twist shrinkage yielded by twisting a yarn is increased exponentially with the increase of the number of twists and where a very high degree of twist is imparted to a yarn, the actual number of twists can be estimated from the twist shrinkage with high accuracy.

Figures 1, 2:
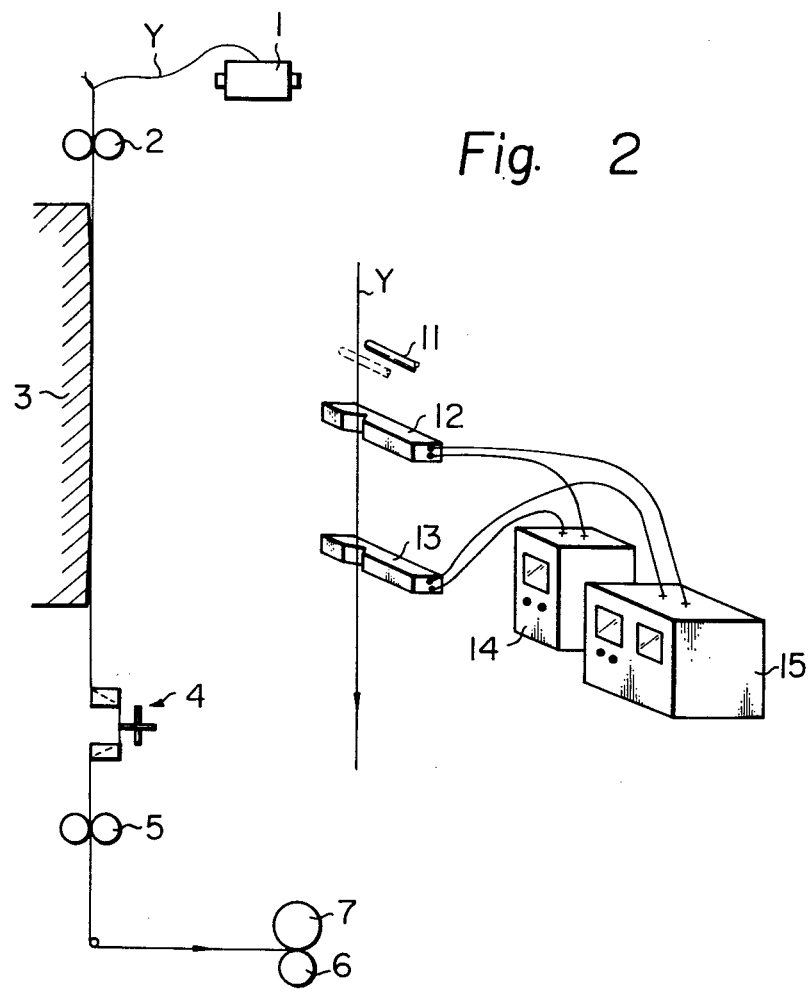
FIG. 1 is a side view schematically illustrating a false-twisting apparatus.
FIG. 2 is a perspective view illustrating a yarn speed measuring device.

Referring now to FIG. 1, a thermoplastic synthetic yarn Y is taken out of a yarn package 1 and fed to a twisting zone by means of a feed roller 2. In the twisting zone, the yarn is heated by a heater 3 while being twisted by a false-twisting means 4 and, thus, the twist given to the yarn is thermally set and fixed. Then, the yarn arrives, while being untwisted, at a delivery roller 5 and, then, is formed into a package 7 by a take-up means 6. Optionally, an undrawn yarn may be fed and, then false twisted while being concurrently drawn. The false-twisting apparatus may also comprise a second heater. The yarn passed through the feed roller 2 is fed to the twisting zone, formed between the feed roller 2 and the false-twisting means 4, at the peripheral speed of the feed roller, and twist begins to be imparted to the yarn by the twisting action of the false-twisting means immediately after the yarn has passed through the feed roller. As the yarn approaches the false-twisting means, the number of twists imparted to the yarn is increased and, thereby the twist shrinkage of the yarn is increased and, thus, the yarn arrives at the false-twisting means with a speed lowered by the increased twist shrinkage.

Figure 8:
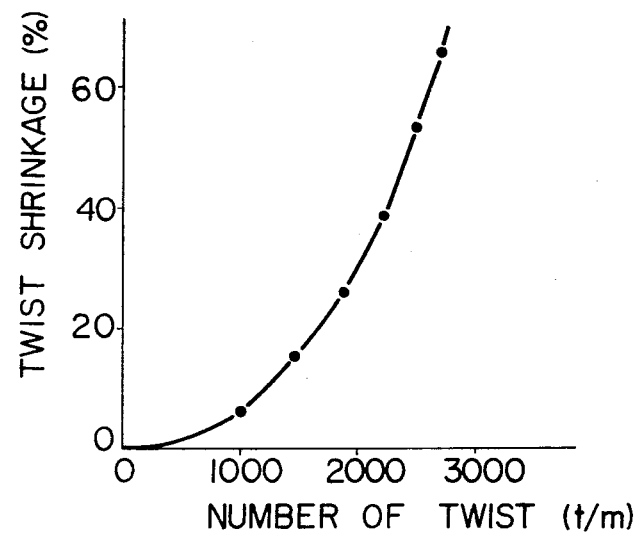
FIG. 8 is a graph of a relationship between the number of twists and twist shrinkage.

Thus, the twist shrinkage can be obtained by measuring, in a certain section of the twisting zone, a speed (V) of the yrn being processed under a normal operational condition and a speed (Vo) of the yarn being processed under the same condition as the normal operational condition but without twisting and calculating according to the following equation:

$$S = \frac{Vo - V}{Vo} \times 100 \tag{1}$$

wherein S is twist shrinkage in percent. From the obtained twist shrinkage, the number of twists of the yarn being normally processed and in the section wherein the yarn speeds (V) and (Vo) were measured can be evaluated in the light of a relationship, as shown in FIG. 8, between the number of twists and twist shrinkage. This relationship may be conveniently obtained by imparting twists to a sample of the yarn to be processed and measuring the twist shrinkage caused by the twists, under a constant tension identical to the tension under which the yarn is normally processed.

The relationship between number of twists and twisting shrinkage can be represented by the following equation:

$$Y = \alpha S^\beta \tag{2}$$

wherein Y is number of twists and $\alpha$ and $\beta$ each is a constant and, therefore, it is easily understood that the number of twists can be (Vo) from the twist shrinkage.

The number of twists actually imparted to the yarn being processed can also be determined from the passing time of the yarn through the section wherein the yarn speeds (V) and (Vo) were measured. This will be appreciated from the following equation which is rewritten from the above equation (1).

$$S = \frac{T - To}{T} \times 100 \tag{3}$$

wherein T is the passing time of the yarn at the speed (V) through the yarn speed measuring section and To is the passing time of the yarn at the speed (Vo) through the same section. As is seen from the above equation (3), the twist shrinkage (S) is a function of the passing time (T) and, therefore, it will also be appreciated that the number of twist can be determined by using the measured passing time (T) from the above equations (2) and (3).

The measurement of the yarn speed during false-twisting operation can be carried out by various methods. The methods usable for the measurement can be divided into two types, one of which is a type wherein a yarn speed is measured without the yarn being brought into contact with any portion of the yarn speed measuring device and the other is a type wherein a yarn speed is measured under a condition such that the yarn is in contact with a part of the yarn speed measuring device.

The former type of method for measuring the yarn speed during the false-twisting operation is carried out by applying a marker, which is detectable by a yarn speed measuring device, to a yarn being processed and measuring by means of the yarn speed measuring device the time it takes for the marker to pass through a prescribed distance in the progressive direction of the yarn. The marker applied to the yarn is detected by a sensing head of the yarn speed measuring device and the yarn speed is evaluated from the marker's passing time through the prescribed distance. Thus, it is advantageous to detect a change generated by the marker and convert it into a pulse at the time when the first end of the applied marker passes through the sensing head. The yarn speed measuring device may detect the marker for example by electrical, magnetic, optical or radioactive action.

Thus, in one form of the invention, the yarn speed measuring device shown in FIG. 2 can be advantageously utilized. This device comprises two sensing heads 12, 13 which can detect a marker on the yarn as a change of dielectric constant, and are spacedly disposed along the path of the yarn Y, and a bar 11, for applying the marker capable of varying the dielectric constant of the yarn, disposed upstream of the sensing heads. This bar is movable in such a way that the bar can be brought into contact with and removed from the yarn. The bar 11 is brought into contact with the yarn Y, fed from a yarn package through a feed roller of a false-twisting apparatus as shown in FIG. 1, and thereby the marker, capable of varying the dielectric constant of the yarn, is applied to the yarn. The sensing heads 12, 13 disposed at a proper interval and in series along the path of the yarn detect the change of dielectric constant as an electrical change. Sensing heads having dielectric constant change detecting efficiency substantially identical to each other may be suitably employed. The two electric changes detected by the two sensing heads are then applied to a counter 15 which is electrically connected to the sensing heads and, thereby the passing time of the marker applied to the yarn through the two sensing heads is measured to evaluate the yarn speed. More specifically, the change of dielectric constant detected by the sensing head 12 is converted into a pulse and, then, the counter 15 begins to count. When the yarn has been advanced and the marker on the yarn has passed through the sensing head 13, the sensing head 13 also generates a pulse and the pulse is applied to the counter 15 and then, the counter stops counting. The count of the counter can be converted into time in miliseconds or of microseconds. Thus, the passing time of the marker on the yarn, i.e. a certain point of the yarn, through the sensing heads is measured and, thereby, the yarn speed is determined from the passing time and the distance between the two sensing heads. Shown by 14 is a controller for the sensing heads including pulse amplifiers.

Figure 3:
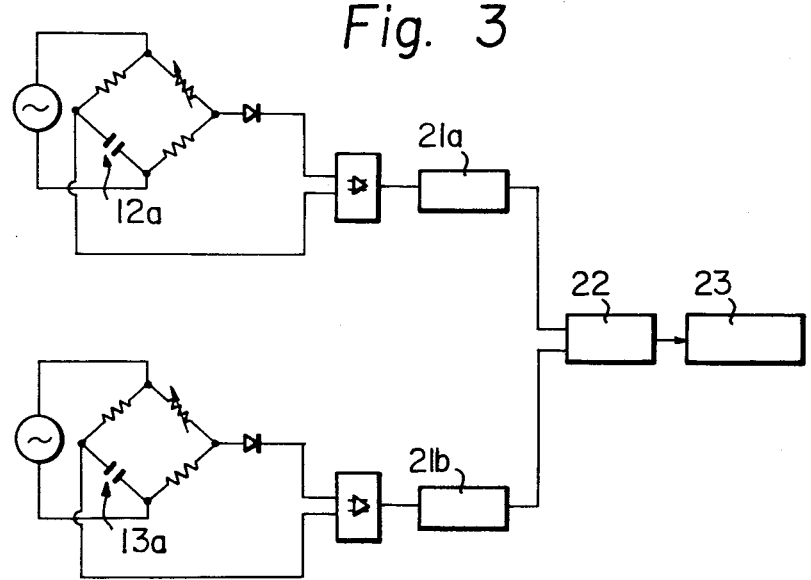
FIG. 3 is a diagram of the yarn speed measuring device shown in FIG. 2.

A diagram of the yarn speed measuring device shown in FIG. 2 is specifically shown in FIG. 3. The sensing head portion of the device comprises a high-frequency generator, a condenser included in a bridge, a rectifier and an amplifier. Thus, when the marker on the yarn passes between the two electrodes of the condenser 12a, as well as the electrodes of the condenser 13a, the voltage is changed. This change is detected as a pulse which is then rectified, amplified and, thereafter, applied to the counter portion of the device. The counter portion comprises two shaping circuits 21a, 21b connected to each of the two sensing head portions, a counting circuit 22 and a display 23. The pulse detected by the condenser 12a (sensing head 12) and applied to the counter portion is shaped by the shaping circuit 21a and the counting circuit 22 is started to count, while the pulse detected by the condenser 13a (sensing head 13) is shaped by the shaping circuit 21b and the counting is stopped. Thus, the time of the marker's passing time through the sensing heads, i.e. the yarn speed, may be displayed on the display 23.

As a marker capable of varying the dielectric constant of a yarn to be processed, liquids such as water, oils or thickener solutions may be conveniently used. Other materials having a dielectric constant different from that of the yarn, such as carbon or metal powders, may also be employed. Among these materials, highly viscous oils and thickener solutions are preferably employed because these materials have little drawback that the detection of the change of dielectric constant may become difficult owing to the scattering of the applied material by centrifugal force cause by the rotation of the yarn. The use of solid materials such as carbon and metal powders may be employed as a suspension in a suitable medium. Further, spinning oils and coning oils may be employed as the marker. However, where oils are used which are of the same quality as that of the oil applied to the yarn in a previous step such as a spinning step, it is advantageous to apply such oils in a fairly large amount.

Instead of two sensing heads, one sensing head can be employed. In this case, a counter is started at the time of the contact of the marker applying means with the yarn and is stopped by the pulse generated by the sensing head.

Other known devices may also be utilized for detecting a marker on the yarn. Thus, the combination of a sensing head and a marker may include, for example, an induction coil in combination with a metal material, a photo-electric device in combination with a coloring or metal material and a Geiger counter in combination with a radioactive material. Also, the combination of a static voltage detector and an electrostatic charge applied to the yarn, for example, by a high tension electrode may be advantageously utilized. The changes detected by these combinations may also be converted into pulses and applied to a counter in a similar manner as mentioned for the device shown in FIGS. 2 and 3.

Another type of method for measuring the yarn speed during a false-twisting operation is carried out under a condition such that the yarn is in contact with a yarn speed detecting roller. The number of rotations of the detecting roller, which is rotated by friction between the surface of the detecting roller and the yarn being processed, is measured electrically, optically or mechanically. In this case, signals generated by each rotation of the detecting roller may also be applied to a counter. This type of method is well known and may be conveniently utilized for the practice of the invention. However, of the above described types of methods it is preferred to employ the former type of method for measurement of the yarn speed, because in the latter type of method, noticeable error may appear by slippage and the quality of the resultant yarn may be affected by the contact of the yarn with the detecting roller.

Heating for thermal set of the twist and have little or no effect on the twist shrinkage determined from the equation (1), above, based on the yarn speeds measured under a normal operational condition with and without twisting, and this is an advantage of the invention.

The twist shrinkage thus determined is extrapolated into the relationship between number or twists and twist shrinkage, as shown in FIG. 8, which has been determined for the yarn to be processed, to estimate the number of false twists actually imparted to the yarn. The relationship between number of twists and twist shrinkage may be manually determined, for example, by twisting a yarn to be processed by means of a twist counter and measuring the twist shrinkage of the twisted yarn. The twisting and the measuring are both carried out under a constant tension identical to the tension under which the yarn is normally processed.

For measurement of the yarn speed during the time the yarn is being processed on a false-twisting apparatus, it is possible to measure the yarn speed in any section in the twisting zone, such as a section between a feed roller and a heater or between a heater and a false-twisting means. In the case where such a relationship as shown in FIG. 8 is to be employed, it is generally preferred to measure the yarn speed in a section between a heater and a false-twisting means. This is because, in such a section, the number of twists imparted to the yarn by the false-twisting means is largest and, thus, the estimation of the number of twist can be effected with high accuracy. However, in such a section, the yarn is rotated more rapidly than the yarn in a section between a feed roller and a heater and, thus, the measurement of the yarn speed may become difficult owing to the ballooning of the yarn. Therefore, in such a case, it may be necessary to measure the yarn speed in a section between a feed roller and a heater.

It has been found from experiments that, according to the equation (2), above, a predetermined number of false twists (Yo) can be represented by the equation:

$$Y_o = \alpha S^\beta + \gamma \tag{4}$$

wherein $\gamma$ is a constant. Therefore, if the constants $\alpha$, $\beta$ and $\gamma$ have been previously determined in experimental tests by determining the twist shrinkage in a section between a feed roller and a heater, the number of false twists actually imparted to the yarn can also be estimated with high accuracy from the determined twist shrinkage according to the relationship of the equation (4) even when the yarn speed is to be measured in such a section.

Using the number of false twists thusly estimated, the false twisted yarns can easily be quality controlled, for example, by separating them into lots based on the detected differences in the number of false twists along the yarn length or between two or more of the false-twisting means. However, it is also possible to control the number of false twists being imparted to the yarn by regulating the difference between the predetermined number of false twists and the estimated number of false twists.

Figure 4:
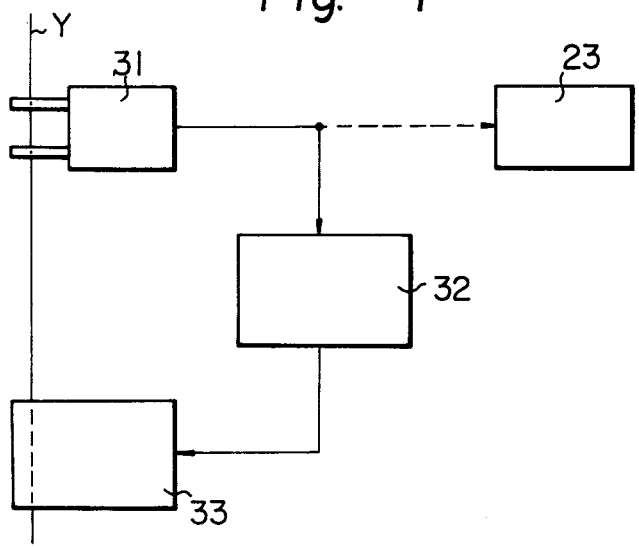
FIG. 4 is a block diagram of a system for measuring a yarn speed and controlling the number of false twists.

Referring to FIG. 4, the yarn speed detected by the yarn speed measuring device 31 is converted into an electrical signal of the number of twists and applied to the controller 32. Then, the number of twists of the applied signal is compared by the controller to the predetermined number of twists and the difference between the determined number of twists and the predetermined number of twists is applied as a control signal to the regulating device 33 to regulate the number of false twists being imparted to the yarn. In the drawing, Y represents the yarn being processed and 23 represents a display.

For the regulation of the number of false twists being imparted to the yarn, various measures may be employed. Firstly, in the case where a false-twisting spindle unit is employed as the false-twisting means, the number of false twists being imparted may be regulated by varying the number of rotations of a motor for driving the spindle unit. Secondly, in the case where a fluid jet type false-twisting unit is employed, the number of false twists may be regulated by varying the air pressure to be applied to the false-twisting unit. Thirdly, in the case where a friction type false-twisting unit is employed, the number of twists may be regulated by varying the number of rotations of the false-twisting unit or by varying the lap angle at a section wherein the yarn is in contact with the false-twisting means. Though the number of false twists may be regulated by varying the yarn speed in any of the above-mentioned cases, it would be disadvantageous to slow down the yarn speed due to the resulting decrease in productivity.

Figure 5:
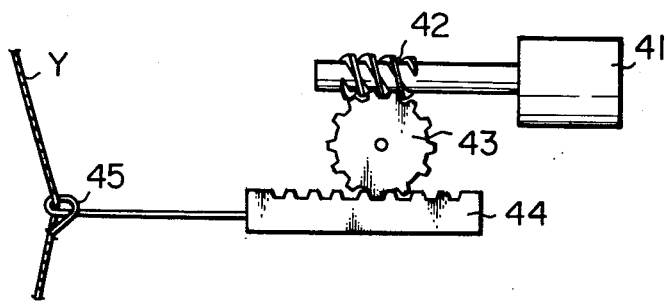
FIG. 5 is a side view illustrating a device for controlling the number of false twists.
Figure 6:
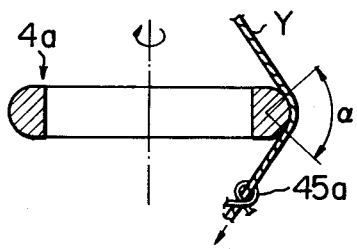
FIGS. 6 and 7 are views schematically illustrating mechanisms for controlling the number of false twists.
Figure 7:
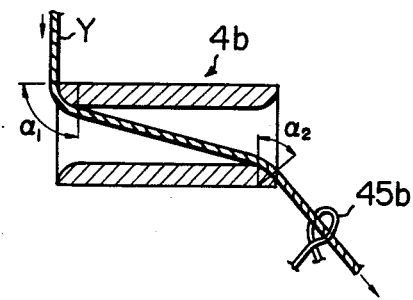

A specific embodiment of the device for the regulation of the number of false twists, wherein the lap angle is varied, is shown in FIG. 5. A control signal (voltage) generated from a controller is applied to the servomotor 41, the rotation of the servomotor is directly communicated to the worm 42 connected to the servomotor and, thus, the worm wheel 43 is rotated and the rack 44 is moved linearly in the longitudinal direction. The rack is connected to a yarn guide for varying the lap angle and, thus, since the lap angle is varied by the rotation of the servomotor 41, number of false twists being imparted to the yarn Y can be regulated thereby based on the application of the control signal. Referring to FIGS. 6 and 7, it will be clearly understood that the lap angle can be varied by the linear movement of the yarn guide 45a (45b). In FIG. 6, the friction disc type twister 4a is in contact with the yarn Y at a lap angle $\alpha$ and the lap angle is changed by the linearly movable yarn guide 45a. In FIG. 7, the friction bush type twister 4b is in contact with the yarn Y at a lap angle $(\alpha_1 + \alpha_2)$ and the lap angle is changed by the yarn guide 45b. Further, it will be appreciated that the lap angle in the case where a friction bush type twister is employed may be changed by varying the direction of the axis of rotation of the twister and that the lap angle in the case where a friction rope type twister or the like is employed can also be changed in a similar manner as mentioned above.

For varying the lap angle, a torque balance mechanism such as a torque motor and an oil pressure mechanism such as an oil pressure cylinder may also be advantageously employed.

Further, it will be appreciated that for the control of the number of false twists being impartd to the yarn, it is also possible to employ a relationship as represented by the equation (4), above, and to regulate the passing time of the yarn through a section within the twisting zone. The relationship usable in such a case may be determined, for example, by taking out the yarn in the section wherein the yarn passing time was measured and measuring the twist shrinkage of the taken out yarn and, thus, determining the constants $\alpha$, $\beta$ and $\gamma$. In this way, the relationship between yarn passing time and predetermined number of false twist can be obtained and by means of this relationship the number of false twists being imparted to the yarn can be controlled by regulating the passing time of the yarn through the section.

In accordance with the invention, it becomes possible to control the quality of the obtained false twisted yarns by separating them into lots according to the determined number of false twists and, moreover, to control with high accuracy the number of false twists being imparted. Thus, false twisted yarns of even and high quality can be provided and, further, an increase in the processing speed of the false twisting can be easily effected.

The features of the invention will now be more distinctly illustrated by the following illustrative, but not limitative examples.

EXAMPLE 1

Drawn polyethylene terephthalate multifilamentary yarn of 150 deniers/30 filaments was used as a material yarn.

Yarn samples of the quality were twisted by a twist counter under a tension of 0.1 g/d and the twist shrinkages of the twisted yarns were determined under the same tension. The number of twists imparted to the yarn and the twist shrinkage of the twisted yarn were plotted for each of the sample yarns and a relationship between number of twists and twist shrinkage was obtained. The graph of the obtained relationship is shown in FIG. 8.

The material yarn was false twisted on an apparatus such as illustrated in FIG. 1, but the apparatus was provided with a conventional false-twisting spindle unit as the false-twisting means. The false twisting was carried out under the following conditions and at various yarn delivery speeds while maintaining the number of rotations of the spindle constant.

| | |
|---|---|
| Number of rotations of spindle | 210,000 r/m |
| Temperature of heater | 210° C |
| Overfeed percentage | +2.2 |

Yarn speeds in a section between the heater and the spindle were measured during the time the yarn was being processed under the above conditions at the respective yarn delivery speeds. Also, yarn speeds in the same section were measured during the time the yarn was being processed without twisting under the above conditions at the respective yarn delivery speeds. The measurement of the yarn speed was carried out by means of a freely rotatable grooved roller where the yarn was once turned onto the grooved roller and the yarn speeds were detected as the number of rotations of the roller.

Then, twist shrinkages at the respective yarn delivery speeds were evaluated from the detected numbers of rotations of the roller. After that, the twist shrinkages were extrapolated into the relationship shown in FIG. 8 and, thus, the numbers of false twists were estimated. Results are shown in Table 1 below.

Table 1

| Run No. | Predetermined number of twists (t/m) | Vo (r/m) | V (r/m) | Twist shrinkage (%) | Estimated number of twists (t/m) |
|---|---|---|---|---|---|
| 1 | 1,800 | 1,760 | 1,364 | 22.5 | 1,785 |
| 2 | 2,000 | 1,597 | 1,110 | 30.5 | 1,975 |
| 3 | 2,200 | 1,450 | 880 | 39.2 | 2,190 |
| 4 | 2,400 | 1,330 | 685 | 48.5 | 2,375 |
| 5 | 2,600 | 1,230 | 535 | 56.5 | 2,570 |

In the above table, Vo represents the number of rotations of the roller detected for the yarn being processed without being twisted and V represents the number of rotations of the roller detected for the yarn being processed with being twisted.

As is evident from the above results, the number of false twists being imparted to the yarn can be easily and accurately estimeated in accordance with the invention during a false-twisting operation.

EXAMPLE 2

Drawn polyethylene terephthalate multifilamentary yarn of 150 deniers/30 filaments was used as a material yarn.

Three types of the material yarns with three different spinning oils applied thereto were false twisted on an apparatus as shown in FIG. 1. This apparatus was provided as the false-twisting means with a friction type false-twisting unit wherein two bush type twister was combined with one disc type twister as an auxiliary twister. The false twisting was carried out under the following conditions while the yarn speed was measured by the yarn speed measuring device as shown in FIG. 2.

| | |
|---|---|
| Number of rotations of bush type twisters | 5,500 r/m |
| Number of rotations of auxiliary twister | 3,500 r/m |
| Temperature of heater | 220° C |
| Overfeed percentage | −3.4% |
| Yarn delivery speed | 150 m/min |

Figure 9:
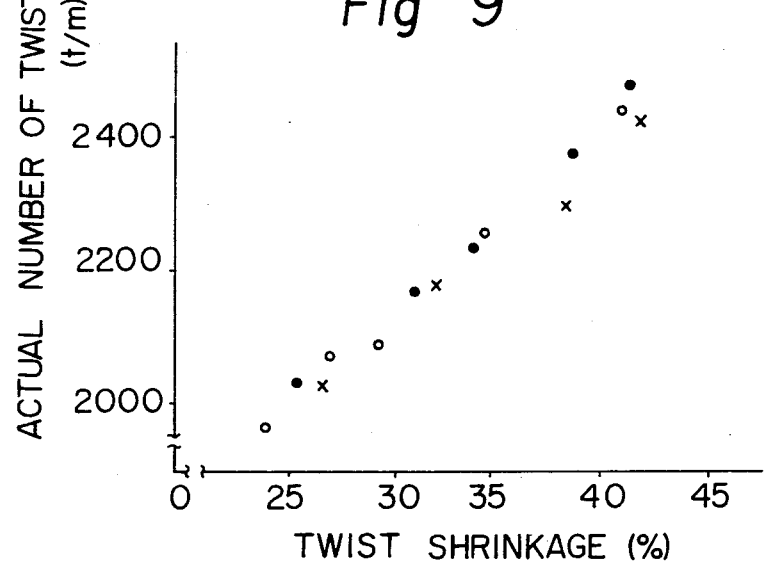
FIG. 9 is a graph of a relationship between twist shrinkage and the actual number of twists.

Water was employed as the marker and two sensing heads were placed in a section between the heater and the false-twisting unit at a distance of 100 milimeters. The number of twists to be imparted to the yarn was changed by varying the lap angle between the yarn and the twisters and the number of twists actually imparted to the yarn was measured by means of a twist counter after taking out the yarn in the section between the two sensing heads; while the twist shrinkage was determined from the measured yarn speed for each of the yarn samples on which the actual number of twist was measured. The results are graphically shown in FIG. 9 wherein o, and x are the measured values for the yarns with the respective spinning oils applied thereto.

From the shown results, it is apparent that the number of false twists can be accurately estimated without being effected by the differences in the type of the applied oils.

EXAMPLE 3

Drawn polyethylene terephthalate multi-filamentary yarn of 150 deniers/30 filaments was false twisted on an apparatus as described in Example 1. The false twisting was carried out under the following conditions and at various numbers of rotations of the spindle.

| | |
|---|---|
| Temperature of heater | 210° C |
| Overfeed percentage | +1% |
| Yarn delivery speed | 120 m/min |

By using a device such as shown in FIG. 2, the passing times of the yarn between the two sensing heads placed at a distance of 100 milimeters were measured in a section between the feed roller and the heater and, then, twist shrinkages were determined from the measured passing times. Then, the numbers of false twists imparted by the respective numbers of rotations of the spindle were estimated from the relationships between the number of twists and the twist shrinkage. The relationships were determined by actually measuring, for each of the respective numbers of rotations of the spindle, the twist shrinkages in the section between the two sensing heads. The results are shown in Table 2 below.

Table 2

| Number of rotations of spindle (r/m) | Predetermined number of twists (t/m) | To (ms) | T (ms) | Twist shrinkage (%) | Estimated number of twists (t/m) |
|---|---|---|---|---|---|
| 276,000 | 2,300 | 496.5 | 546.2 | 9.1 | 2,280 |
| 300,000 | 2,500 | 497.3 | 563.2 | 11.7 | 2,493 |
| 324,000 | 2,700 | 496.8 | 574.3 | 13.5 | 2,690 |

In the above table, To represents the passing time of the yarn being processed without being twisted and T represents the passing time of the twisted yarn being processed.

As is apparent from the above results, according to the invention the number of false twists being imparted to the yarn can be accurately estimated even in a section between a feed roller and a heater.

EXAMPLE 4

Drawn polyethylene terephtharate multi-filamentary yarn of 150 deniers/30 filaments was false twisted on an apparatus as described in Example 1. The false twisting was carried out under the following conditions and at various yarn delivery speeds.

| | |
|---|---|
| Number of rotations of spindle | 215,700 r/m |
| Temperature of heater | 210° C |

The yarn was false twisted at overfeed percentages which could apply tensions of 0.1, 0.2 and 0.3 grams/denier to the processing yarn. At the respective yarn delivery speeds, the twist shrinkages of the yarn being false twisted were actually measured in a section between the feed roller and the heater. The results are shown in Table 3 below.

Table 3

| | | Actually measured twist shrinkage (%) Predetermined number of twists (t/m) | | | | | |
|---|---|---|---|---|---|---|---|
| | | 2,000 | 2,200 | 2,400 | 2,500 | 2,600 | 2,800 |
| Tension (g/d) | 0.1 | 5.7 | 7.7 | 10.1 | 11.5 | 13.0 | 16.2 |
| | 0.2 | 5.0 | 6.8 | 8.9 | 10.0 | 11.3 | 13.9 |
| | 0.3 | 4.7 | 6.3 | 8.1 | 9.1 | 10.2 | 12.5 |

From the results, the constants $\alpha$ and $\beta$ of the equation (4) were calculated. The results are shown in Table 4 below.

Table 4

| Tension (g/d) | 0.1 | 0.2 | 0.3 |
|---|---|---|---|
| $\alpha$ | 618.8 | 632.6 | 634.5 |
| $\beta$ | 0.433 | 0.460 | 0.478 |

$\alpha$ was found to be constant and approximately 675.0.

By using the equations (3) and (4), the relationships between the passing time (T) and the predetermined number of twists were determined from the obtained values of the constants $\alpha$, $\beta$ and $\gamma$. The relationships determined in this way are shown in FIG. 10, wherein the curve A is the relationship under a yarn tension of 0.1 gram/denier, the curve B under a yarn tension of 0.2 grams/denier and the curve C' the relationship under a yarn tension of 0.3 grams/denier.

Figure 10:
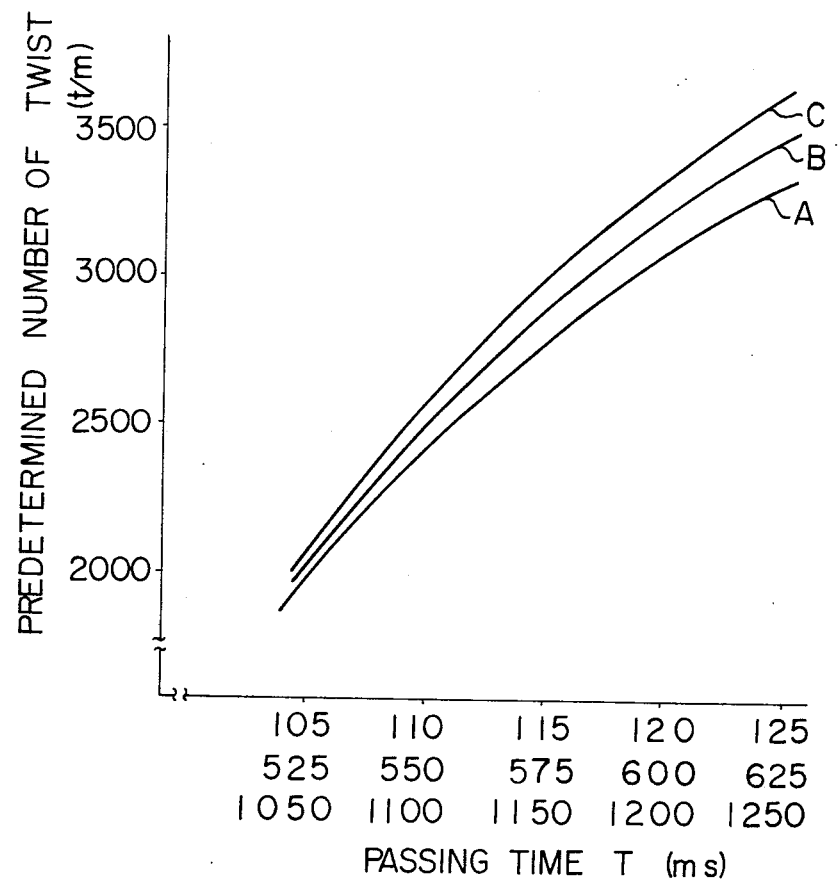
FIG. 10 is a graph of a relationship between a yarn's passing time through a prescribed distance and predetermined number of twists.

As will be appreciated, T is varied by the yarn speed and the distance through which the passing time is measured and, therefore, the abscissa of FIG. 10 is graduated by the shown three orders of T. For example, if the speed of the yarn being processed without being twisted is 120 meters/minute, To is 1,000 miliseconds for the distance of 2,000 milimeters, To is 500 miliseconds for the distance of 1,000 milimeters and To is 100 miliseconds for the distance of 200 milimeters.

By using the relationships between passing time the predetermined number of twists shown in FIG. 10, the predetermined number of twists can easily be regulated from the measured passing time.

EXAMPLE 5

Drawn polyethylene terephtharate multi-filamentary yarn of 150 deniers/30 filaments was false twisted on two types of apparatuses, each being arranged as shown in FIG. 1. One of the apparatuses was provided with five disc type twisters and the other was provided with two bus type twisters. In each case, the false twisting was carried out under the following conditions while the lap angle between the yarn and the twisters was varied.

| | |
|---|---|
| Peripheral speed of twister/yarn speed ratio | 3.5 |
| Temperature of heater | 210° C |
| Overfeed percentage | −2.2% |

Figure 11:
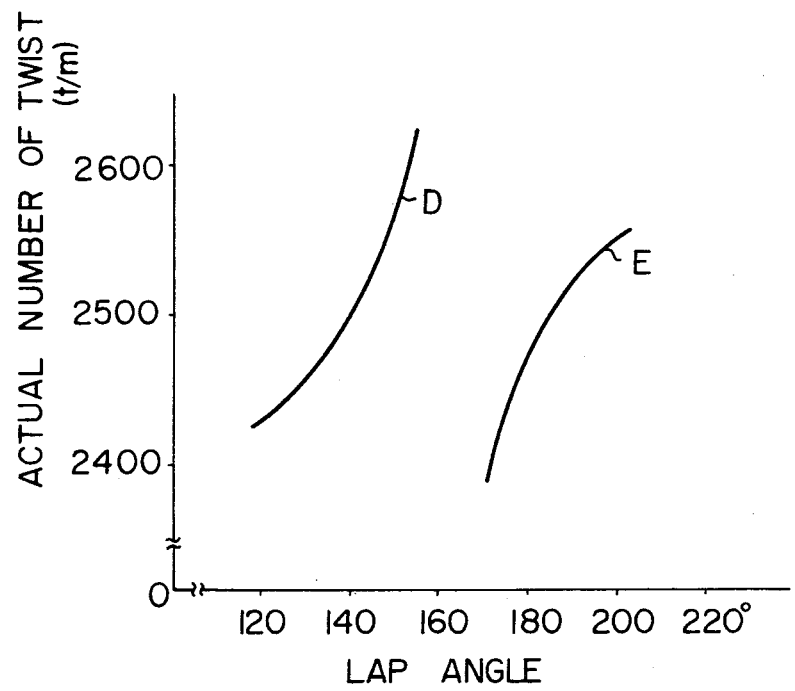
FIG. 11 is a graph of a relationship between the lap angle of a yarn and a friction type twister and the actual number of twists.

The numbers of twists were actually measured at the respective lap angles. The results are shown in FIG. 11 wherein the curve D is the relationship for the bush type twister and the curve E for the disc type twister.

From the results, it will be appreciated that the number of twists being imparted to the yarn by a friction type false-twisting unit can be controlled by regulating the lap angle.

In fact, in the false twisting operation on each of the above-mentioned apparatuses, the number of twists being imparted to the yarn could be easily and accurately controlled by measuring the yarn speed by means of a device as shown in FIG. 2 and regulating the lap angle by means of a device as shown in FIG. 5 through a system as shown in FIG. 4.

What we claim is:

1. A process for false twisting a thermoplastic synthetic yarn wherein a yarn of thermoplastic synthetic fibers is fed through a feed roller, the fed yarn is false twisted by a false-twisting means while being heated and, then, the false twisted yarn is taken up through a delivery roller, which process comprises directly measuring, in a section within the twisting zone formed between the feed roller and the false-twisting means, the speed of the yarn being processed under a normal operational condition with twisting to estimate the number of false twists actually imparted to the yarn by determining twist shrinkage of the yarn in said section from the measured yarn speed and the speed of the yarn being processed under the same condition as said normal operational condition but without twisting, which is measured in the same section as that wherein said speed of the yarn being processed under the normal operational condition with twisting has been measured and, then, estimating the number of twists from the determined twist shrinkage.

2. A process as claimed in claim 1, comprising applying a marker, which can be detected by a yarn speed measuring device, to the yarn being processed, and said step of measuring comprises measuring by means of the yarn speed measuring device the time it takes for the marker to pass through a prescribed distance of said section.

3. A process as claimed in claim 2, wherein said combination of a marker with a yarn speed measuring device is selected from the combinations comprising a condenser with a material capable of varying the dielectric constant of the yarn, an induction coil with a metal material, a photo-electric device with a coloring or metal material, a Geiger counter with a radioactive material and a static voltage detector with an electrostatic charge.

4. A process as claimed in claim 1, wherein said yarn speeds are measured by bringing a freely rotatable roller in contact with the yarn in said section and measuring the number of rotations of the roller which is rotated by friction between the surface of the roller and the yarn being processed.

5. A process as claimed in claim 1, which further comprises controlling the number of false twists being imparted to the yarn by regulating the difference between a predetermined number of false twists and the estimated number of false twists.

6. A process as claimed in claim 5, wherein said number of false twists being imparted to the yarn is controlled by varying the number of rotations of a motor for driving the false-twisting means, varying the air pressure to be applied to the false-twisting means or varying the lap angle at a section wherein the yarn is in contact with the false-twisting means.

7. The process of claim 1 comprising determining the relationship between the number of twists and the twist shrinkage of a yarn to be false twisted, whereby said step of estimating comprises extrapolating said determined twist shrinkage into said relationship to estimate the number of actual twists in the false twist yarn.

8. An apparatus for false twisting a thermoplastic synthetic yarn comprising a feed roller for feeding a yarn, a heater for thermally setting the twist imparted to the yarn, a false-twisting means for imparting false twists to the yarn and a delivery roller for advancing the yarn to a take-up means, and which further comprises a device for measuring, in a section within the twisting zone formed between the feed roller and the false-twisting means, the speed of the yarn being processed, and a device for controlling the number of false twists being imparted to the yarn in response to said measuring device.

9. An apparatus as claimed in claim 8, wherein said yarn speed measuring device comprises a sensing head for detecting a marker applied to the yarn.

10. An apparatus as claimed in claim 9, wherein said sensing head is a member selected from the group consisting of a condenser for detecting a dielectric constant variable material, an induction coil for detecting a metal material, a photo-electric device for detecting a coloring or metal material, a Geiger counter for detecting a radioactive material and a static voltage detector for detecting an electrostatic charge.

11. An apparatus as claimed in claim 8, wherein said yarn speed measuring device comprises a detecting roller rotatable by friction between the surface of the roller and the yarn being processed.

12. An apparatus as claimed in claim 8, wherein said device for controlling the number of false twists comprises a yarn guide, for varying a lap angle at a section wherein the yarn is in contact with the false-twisting means, said yarn guide being connected to a servometer through a worm gear and a rack so that the lap angle is varied by the linear movement of the guide.

13. An apparatus as claimed in claim 8 wherein said device comprises means responsive to the output of said speed measuring means for controlling said false twisting means to impart a determined number of false twists to said yarn.

* * * * *

UNITED STATES PATENT OFFICE
CERTIFICATE OF CORRECTION

Patent No. 4,050,225              Dated  September 27, 1977

Inventor(s)   Meiji Anahara, et al

It is certified that error appears in the above-identified patent and that said Letters Patent are hereby corrected as shown below:

Column 3, line 51:   Change "yrn" to --yarn--.

Column 4, line 12:   Change "(Vo)" to --determined--.

Column 6, line 40:   After "twist" delete --and--.

Column 7, the equation marked (4):   Change "$Y_o = \alpha S^\beta + \gamma$" to -- $Y_o = \alpha S^\beta + \gamma$ --.

UNITED STATES PATENT OFFICE
CERTIFICATE OF CORRECTION

Patent No. 4,050,225     Dated September 27, 1977

Inventor(s) Meiji Anahara, et al

It is certified that error appears in the above-identified patent and that said Letters Patent are hereby corrected as shown below:

Column 11, line 42: Change "$\alpha$" to -- $\gamma$ --.

Column 12, line 4: Change "bus" to --bush--.

Column 14, line 27: Change "servometer" to --servomotor--.

Signed and Sealed this

Twenty-third Day of May 1978

[SEAL]

Attest:

RUTH C. MASON
Attesting Officer

LUTRELLE F. PARKER
Acting Commissioner of Patents and Trademarks